US009480454B2

(12) United States Patent
Shtalryd (10) Patent No.: US 9,480,454 B2
(45) Date of Patent: Nov. 1, 2016

(54) SYSTEMS AND METHODS OF MOVEMENT SENSING BASED MONITORING

(76) Inventor: Haim Shtalryd, Ness Ziyona (IL)

( * ) Notice: Subject to any disclaimer, the term of this patent is extended or adjusted under 35 U.S.C. 154(b) by 1037 days.

(21) Appl. No.: 13/616,597

(22) Filed: Sep. 14, 2012

(65) Prior Publication Data

US 2013/0072764 A1    Mar. 21, 2013

Related U.S. Application Data

(60) Provisional application No. 61/534,994, filed on Sep. 15, 2011.

(51) Int. Cl.
    *A61B 5/08*      (2006.01)
    *A61B 7/00*      (2006.01)
    *A61B 5/113*     (2006.01)
    *A61B 5/00*      (2006.01)

(52) U.S. Cl.
    CPC ............... *A61B 7/003* (2013.01); *A61B 5/08* (2013.01); *A61B 5/113* (2013.01); *A61B 5/002* (2013.01); *A61B 5/746* (2013.01); *A61B 2503/04* (2013.01)

(58) Field of Classification Search
    CPC ........ A61B 7/003; A61B 5/113; A61B 5/08; A61B 5/746; A61B 5/002; A61B 2503/04
    See application file for complete search history.

(56) References Cited

U.S. PATENT DOCUMENTS

| 5,265,619 A | * | 11/1993 | Comby | A61B 5/1101 |
| | | | | 600/595 |
| 5,271,412 A | * | 12/1993 | Shtalryd | A61B 5/113 |
| | | | | 600/529 |

* cited by examiner

*Primary Examiner* — Michael Kahelin
*Assistant Examiner* — Tho Tran
(74) *Attorney, Agent, or Firm* — Leber Patent Law P.C.

(57) ABSTRACT

A system for monitoring characteristics of a subject including a sensor unit including an upper plate, a lower plate, a transducer sensor and an abutting element, which is configured for abutting a surface of the transducer surface, correspondently to forces applied upon the upper plate by the subject and a control unit, for identifying breathing related alarm situations using the sensor unit signals. The system optionally also includes remote devices allowing multidirectional communication between the control unit and each respective remote device and between the remote devices and optionally also enable turning one of these remote devices into a relay station for expanding communication range. The system optionally also includes a mechanical adjustment mechanism connected to the abutting element, for enabling a user to adjust sensitivity of the transducer sensor by mechanically adjusting location of the abutting element in relation to an effective area of the transducer sensor.

3 Claims, 4 Drawing Sheets

SYSTEMS AND METHODS OF MOVEMENT SENSING BASED MONITORING

CROSS-REFERENCE TO RELATED PATENT APPLICATIONS

This application claims priority to Provisional patent application No. 61/534,994 filed on Sep. 15, 2011, which is incorporated herein by reference in its entirety.

FIELD OF THE INVENTION

The present invention generally relates to systems and methods for monitoring physical characteristics of subjects such as human subjects.

BACKGROUND OF THE INVENTION

Monitoring systems and devices for monitoring breathing activity of human subjects and especially for apnea detection of babies, typically monitor a breathing pattern of the subject and operate an alarm mechanism in case breathing irregularity is detected.

Some systems for monitoring baby breathing use movement sensing for identification of breathing of the subject. These systems include one or more sensor-platforms placed underneath the baby's mattress to monitor his/her breathing related movements while the baby is asleep, and one or more control devices that usually hang over the subject's bed. These platforms usually include a lower plate and a covering upper plate, where a piezoelectric sensor and a flexible mediating element such as a rubber/elastomeric element are positioned there-between. The mediating element mediates between the upper plate and piezoelectric sensor to avoid erosion of the surface of the sensor and soften the impact upon the piezoelectric sensor surface, which can lose its sensitivity if not maintained in that way.

The rubber element receives the movements of the subject applied upon the upper plate and transmits them to the piezoelectric transducer, which in turn converts the mechanical force applied thereon into a corresponding electric signal. The rubber element is typically attached to the inner side of the upper plate such that it will interface the piezoelectric surface (which is attached to the inner side of the lower plate) at the center of the sensor's surface to allow maximal transmission of mechanical force to be received by the piezoelectric surface.

SUMMARY OF THE INVENTION

According to some embodiments of the present invention, there is provided a system for monitoring breathing and sound of a subject. the system comprises: (i) a movements sensor unit enabling to sense movements indicative of breathing behavior of the subject and output sensor data associated with the sensed movements; (ii) a control unit, which receives the output sensor data, analyzes the sensor data for identification of breathing related alarming situations and for outputting an alarm whenever a respective alarm situation is identified, where the control unit comprises an audio receiver for detecting sounds in proximity to the subject and a wireless transceiver for transmitting and receiving data thereby over at least one wireless communication channel relating to the detected sound and/or the sensed breathing behavior; and (iii) at least one remote devices comprising at least one transceiver for allowing multidirectional communication between the control unit and each respective remote device and between the remote devices, wherein each remote device enables outputting data relating to the detected sound and/or breathing behavior over at least one output device embedded therein. The communication between the remote devices and between each remote device and the control unit is done over the wireless communication channel.

The system optionally comprises at least two remote devices, wherein each remote device includes at least one audio output device for outputting audio signals relating to at least one of: audio signals detected by the audio receiver of the control unit and/or for outputting a sound alarm upon receiving an alarm signal from the control unit, indicative of an identified breathing alarming situation. Each remote device further comprises an audio receiver to allow communication between users through the respective remote devices.

Optionally, at least one of the remote devices enables turning into a relay station for expanding transmission range of the control unit and of other remote devices, wherein each remote device includes a relay mode switch allowing a user to turn on a relay operation mode for relaying signals received thereby, by transmitting signals received from the control unit to the other respective at least one remote device and from each of the respective other remote devices to the control unit, over the wireless communication channel.

According to some embodiments, the control unit enables transmitting and receiving signals over a multiplicity of predefined wireless communication channels each corresponding to a different frequency band.

Optionally, the control unit is operatively associated with at least one of: an illumination device such as a night-light, illuminating an area in which the sensor unit is installed and/or a music player device, wherein the control unit enables controlling features of each of these devices including on/off switching of each device, dimming level of the illumination device and volume level of the music player. The control unit optionally further allows automatic controlling of the operation features of at least one of: said illumination device and music player, according to currently sensed breathing pattern of the subject allowing synchronizing the dimming and/or volume levels to a breathing state of the subject.

According to some embodiments, the control unit comprises: (i) a processing unit comprising the transceiver and a signal analysis module for identification of breathing related alarming situations and for controlling alarm output devices operatively associated therewith; and (ii) a control panel comprising a display unit for visual display of breathing related characteristics and battery status of the control unit, and an input unit for allowing a user to control the system thereby.

Optionally, the display unit comprises an LCD screen or a touch screen, where the touch screen integrates the display and input units.

The system optionally further comprises a temperature sensor operatively connected to the control unit for enabling sensing temperature of an environment that is proximate to the control unit and therefore to the subject, wherein the sensed temperature is indicated in the display unit.

According to some embodiments, each remote device includes operation buttons for allowing a user to: remotely control volume level of audio output of the respective remote device; select a wireless communication channel; control music player options s and/or settings; and/or control remote illumination characteristics.

According to other embodiments of the present invention, there is provided a system for monitoring presence of a subject in a predefined monitored location. The system comprises: (i) at least one sensor unit placed under a predefined laying platform in which the subject can be seated or laid over, enabling sensing movements of the subject by translating forces applied on a surface of the sensor unit into electric signals, where the movements are associated with movements of the subject; and (ii) a control unit enabling receiving sensor unit output signals indicative of the sensed movements, analyzing movements related output data for identifying breathing related movements and placement related movements of the subject, which indicate when the subject has been placed upon or removed from the platform, identifying breathing alarming situations using this analysis and outputting alarm upon identification thereof, and identification of presence periods indicative of the time the subject was laying over the platform, where the control unit further enables saving data relating to identified presence periods.

According to some embodiments, the analysis includes analyzing the amplitude of the sensor unit output signal and identifying a placement signal when the amplitude exceeds a first threshold level A1 and a removal signal when the amplitude exceeds a second threshold level A2, wherein the signal threshold amplitudes are higher than typical breathing related signal amplitudes due to the higher mechanical force applied by the subject's weight upon the sensor unit surface when the subject is placed over the platform or removed therefrom, allowing the control unit thereby to distinguish the breathing related signals from the placement related signals, wherein the presence time is calculated as the time between the identified placement and removal of the respective subject.

Optionally, each such presence period is indicated over the control unit, through a display unit embedded therein.

Optionally, each such presence period is saved along with information indicative of the date and hour of its occurrence, wherein the data can be outputted and indicated at a later time through the control unit. For example, the control unit enables displaying a table showing each saved presence period and its associated information thereover.

Optionally, the control unit enables transmitting data indicative of each presence period and its respective associated information to a remote mobile device of a user over at least one communication link.

According to other embodiments of the present invention, there is provided a system for monitoring breathing related characteristics of a subject. The system comprises: (i) a sensor unit comprising an upper plate, a lower plate, a transducer sensor located over an inner side of the lower plate facing an inner side of the upper plate, and an abutting element, which is movably connected to the inner side of the upper plate facing a surface of the transducer sensor for abutting it correspondently to forces applied upon the upper plate, wherein the respective subject applies force upon the upper plate when laying thereover and thereby enables the upper plate to apply a mechanical force upon the transducer sensor via the abutting element, wherein this force corresponds to breathing movements of the subject, and wherein the transducer outputs electric signals that correspond to this applied force; (ii) a control unit, which receives signals from the sensor unit indicative of movements of the subject, analyzes these signals to identify breathing related alarm situations and operate at least one alarm upon identification of the alarming situation; and (iii) a mechanical adjustment mechanism connected to the abutting element, for enabling a user to adjust sensitivity of the transducer sensor by mechanically adjusting the location of the abutting element in relation to an effective area of the transducer sensor, wherein sensitivity is decreased when the abutting element is distanced from the effective area.

Optionally, the mechanical adjusting mechanism comprises a mechanical adjustor that mechanically connects to the abutting element and a manual adjustment device mechanically connected thereto for allowing the user to manually adjust the sensitivity level of the transducer sensor by moving the manual adjustment device.

According to some embodiments, the mechanical adjustor includes an upper member and a lower member connected one another, wherein the lower member connects to the abutting element and the mechanical adjustor pivotally connects to the upper plate, wherein the positioning of the transducer sensor is constant and unchangeable, in relation to the upper plate, and wherein the abutting element changes its location in respect to the center of transducer sensor when the upper member is rotated, thereby allowing changing the respective location of the abutting member in relation to the effective area of the transducer sensor and thereby adjust sensitivity thereof to forces applied upon the upper plate by the subject.

The manual adjustment device optionally comprises an adjustment scale, which is a depression in upper plate that includes scaling indicators, which also includes stoppers that allow releasably fixating the handle upper member therein to allow discrete adjustment of the transducer sensor sensitivity.

According to some embodiments, the mechanical adjustment mechanism comprises a mechanical adjustor that mechanically connects to the abutting element, a shaft connected to the mechanical adjustor for rotating thereof, and a motor, which allows rotating the shaft for allowing displacement of the abutting element, wherein the motor is controllable through the control user.

DETAILED DESCRIPTION OF THE INVENTION

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention, in some embodiments thereof, provides systems and methods for monitoring various physical characteristic of subjects especially yet not exclusively human subjects such as breathing related characteristics. One of these characteristics relating to breathing of the subject for enabling identification of breathing related irregularities such as sleep apnea or rapid breathing. The system allows setting off an alarm whenever such predefined irregularity is identified.

According to some embodiments, the system includes a sensor unit, which includes a piezoelectric transducer for sensing movements of the subject by converting force applied on a surface thereof caused due to breathing movements of the subject. The sensor unit is placed under a mattress or any other platform upon which the subject is laid or seated for allowing the movement sensing. The system further includes a control unit, which includes power supply of the transducer and itself, indication and alarm devices such as power indication lamps and a speaker for outputting sound alarms and the like. The control unit further includes a processing unit or any other electronic and/or digital device that can process data and/or signals. The processing unit enables receiving output signals of the sensor unit, indicative of the movements of the subject underneath, analyzing the output signal to determine or identify one or more predefined physical characteristics of the subject such as predefined breathing irregularities such as apnea (no-breathing) situations and/or rapid breathing patterns and to operate the alarm when such irregularities are identified.

According to some embodiments, the sensor unit includes an upper and a lower plate, the piezoelectric transducer having a predefined effective sensitivity area and an abutting element. The piezoelectric transducer is attached to an inner side of the lower plate and the abutting element is attached to an inner side of the upper plate. The upper plate receives the movements of the subject lying thereupon and the attached abutting element is configured to abut an upper surface of the piezoelectric transducer sensor whenever a force is applied upon the upper plate. The abutting element may be positioned to face the center of piezoelectric transducer sensor upper surface, which is typically the spot of the highest sensitivity. This means that the farther the abutting of the abutting element is from that central location or central area of the piezoelectric transducer sensor surface, the lower the sensitivity of the sensor to the forces applied thereon and therefore.

According to additional or alternative embodiments of the present invention, the system further includes a multiplicity of remote devices, each including at least one transceiver for allowing multidirectional communication between the control unit and each respective remote device and between the remote devices themselves. According to some embodiments, the control unit receives the output sensor data, analyzes it for identification of breathing related alarming situations such as breathing cessation or rapid breathing and for outputting an alarm whenever a respective said alarm situation is identified. Additionally, the control unit includes an audio receiver such as a microphone for detecting sounds in proximity to the subject e.g. if the control unit is configured to be hung or positioned in any other manner near the baby's bed where the sensor unit is placed under the baby's mattress, and a wireless transceiver (such as a radio frequency (RF) transceiver) for transmitting and receiving data thereby over at least one wireless communication channel to and from the remote devices. The data may include the detected sound and/or signals indicative of a breathing alarm.

According to some embodiments, each remote device enables outputting data relating to the detected sound and/or breathing behavior over at least one output device such as an audio speaker, embedded therein, wherein the communication between the remote devices and between each remote device and the control unit is done over the wireless communication channel.

The remote devices may further include audio receivers such as microphones for additionally allowing communication between users thereby. This means that the users may use these devices also as communication devices for communicating with one another thereby. For example, in case the system is used for baby monitoring, the remote devices may serve as an additional intercom system for allowing the parents or any other caretakers to aurally communicate with one another or with the subject (e.g. allowing talking to the baby to calm him down from a remote location), while still allowing transmitting and outputting sounds picked from the bed area of the baby and/or output breathing alarms.

Optionally, each of the remote devices may include a relay mode switch that allows the respective remote device to serve as a relay station for the other remote devices for extending transmission range of the control unit, allowing thereby the control unit to transmit a "low signal" meaning a signal of low amplitude for reducing radiation in proximity to the baby.

The analysis of the signals outputted by the sensor unit indicative of sensed movements of the subject, placed thereupon, may additionally or alternatively include identification of presence periods, each defined as the time interval in which the subject has been laying in bed or any other facility upon which the sensor unit is placed. Each presence period is identified by identification of movement patterns or signals indicative of events in which the subject is placed or laid upon the sensor (and e.g. from bed) and events in which the subject is taken out or away from the sensor (e.g. from bed). Each such event may be identified by identifying a distinguishing movement signal associated with breathing related movements of the subject impose a different mechanical impact and force upon the transducer sensor than forces applied due to placing of the subject or taking him/her away from the senor. The placing and taking out (also referred to hereinafter as removing) impose a much higher force upon the transducer sensor than the breathing movements and therefore are distinguishable by much higher amplitude and/or a different frequency pattern. This allows the control unit to identify whenever the subject such as a baby is placed in bed and/or removed therefrom and thereby calculate and register the time there-between as the respective presence period. Additionally or alternatively, the placement/removal events can also be deduced from the breathing signal itself, since the subject's breathing pattern may also vary as a result of being taking out of bed, for instance, or placed therein. This process may allow caretakers such as the baby's parents to follow sleeping periods of their baby, for example.

Figure 1:
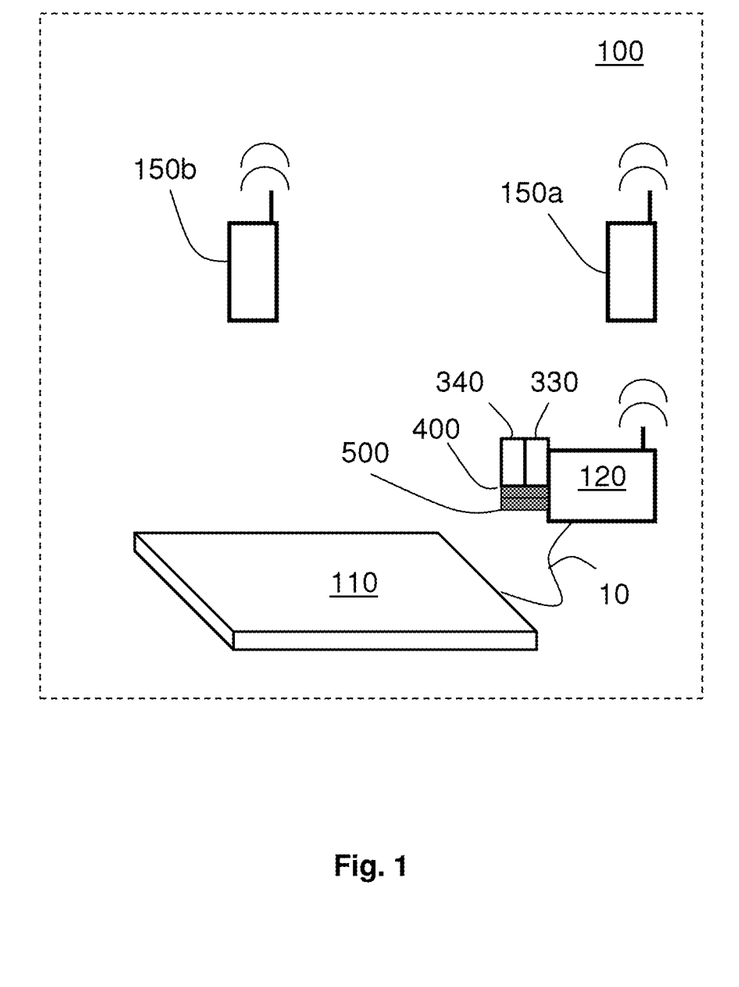
FIG. 1 schematically shows a system for monitoring physical characteristic of a subject including a sensor unit, a control unit and two remote devices, according to some embodiments of the present invention.

Additionally or alternatively, the system further includes a mechanical adjustment mechanism for allowing the user to adjust sensitivity of the transducer sensor by mechanically controlling the positioning of the Reference is now made to FIG. 1, which schematically shows a system 100 for monitoring physical characteristic of a human subject including a sensor unit 110, a control unit 120 and two remote devices 150a and 150, according to some embodiments of the present invention. Sensor unit 110 is a piezoelectric based sensor unit including an upper plate, a lower plate, an abutting element and a piezoelectric transducer sensor as described above, each set is cased by the plates in a manner that allows the upper plate and attached abutting element to move in response to the subject's movements. Sensor unit 110 is configured to be placed under a mattress of a baby bed and control unit is designed to be hung over the bed or placed in proximity thereof. Control unit 120 may electronically connect to sensor unit 110 through an electric wire 10 as illustrated in FIG. 1 or wirelessly communicate therewith for transmission of the output signals from the transducer sensor of sensor unit 110 to control unit 120.

Control unit 120 may include devices such as one or more illumination devices such as a night-light 400 that can be switched on/off or dimmed by control unit 120, and/or a music player 500 that can allows the user to control features thereof such as volume level, track selection and the like. According to some embodiments, these devices are remotely situated from control unit 120 and are connected thereto via wired or wireless connection for allowing the user to, for instance, dim and/or switch on/off night-light 400 and the like.

Optionally, control unit 120 enables synchronizing the musical tracks and features thereof with features of the played music, according to predefined default and/or selectable one or more programs. For example, control unit 120 includes a "sleep" mode button, where whenever switched on a default program is operated by control unit 120, in which predefined musical track(s) suitable for relaxing the baby for helping the baby to fall asleep are played where the volume of the music is gradually lowered in synchronization with dimming of night-light 400.

According to some embodiments of the present invention, control unit 120 allows automatic controlling (by changing) of operation features of these added devices such as controlling the dimming level of night-light 500 and/or volume level of the audio player, according to the sensed breathing pattern and/or according to other parameters such as the time of the day and the like, associated with output signal of sensor unit 110, allowing thereby synchronizing the dimming and volume levels to a breathing state of the subject. For example, control unit 120 analysis of the output signal allows identification of breathing patterns that can be associated with sleep stages indicative that the subject (e.g. baby) is falling asleep. The intensity of the light of night-light 400 and/or the volume level of music played by music player 500 may be decreased according to characteristics of the breathing pattern (e.g. according to the decrease rate of the baby's breathing frequency). Optionally, a predefined "causing to sleep" program including predefined automatic decreasing rates for decreasing light intensity and/or volume level is automatically operated by control unit 120 upon identifying that both: (i) the time is between two threshold predefined hours (considered as "night") such as between 07:00 PM and 05:00 AM; as well as (ii) the subject is placed upon sensor unit 110 (is in bed).

According to some embodiments of the present invention, control unit 120 further includes at least one audio output device such as an audio speaker 30 for outputting sound alarms and an audio receiver such as a microphone 40 for detecting sounds in the proximal area of control unit 120 and therefore of the subject.

According to some embodiments of the present invention, each of remote devices 150*a* and 150*b* is a communication device enabling communication with control unit 120 and/or 150*b* and between remote devices 150*a* and 150*b* themselves. This will enables, for instance, users to communicate with one another through remote devices 150*a* and 150*b* as specified above, using them as a multidirectional intercom system while still enabling each remote device 150*a* and/or 150*b* to receive and output sounds detected by control unit 120 (using microphone 40).

Figure 2:
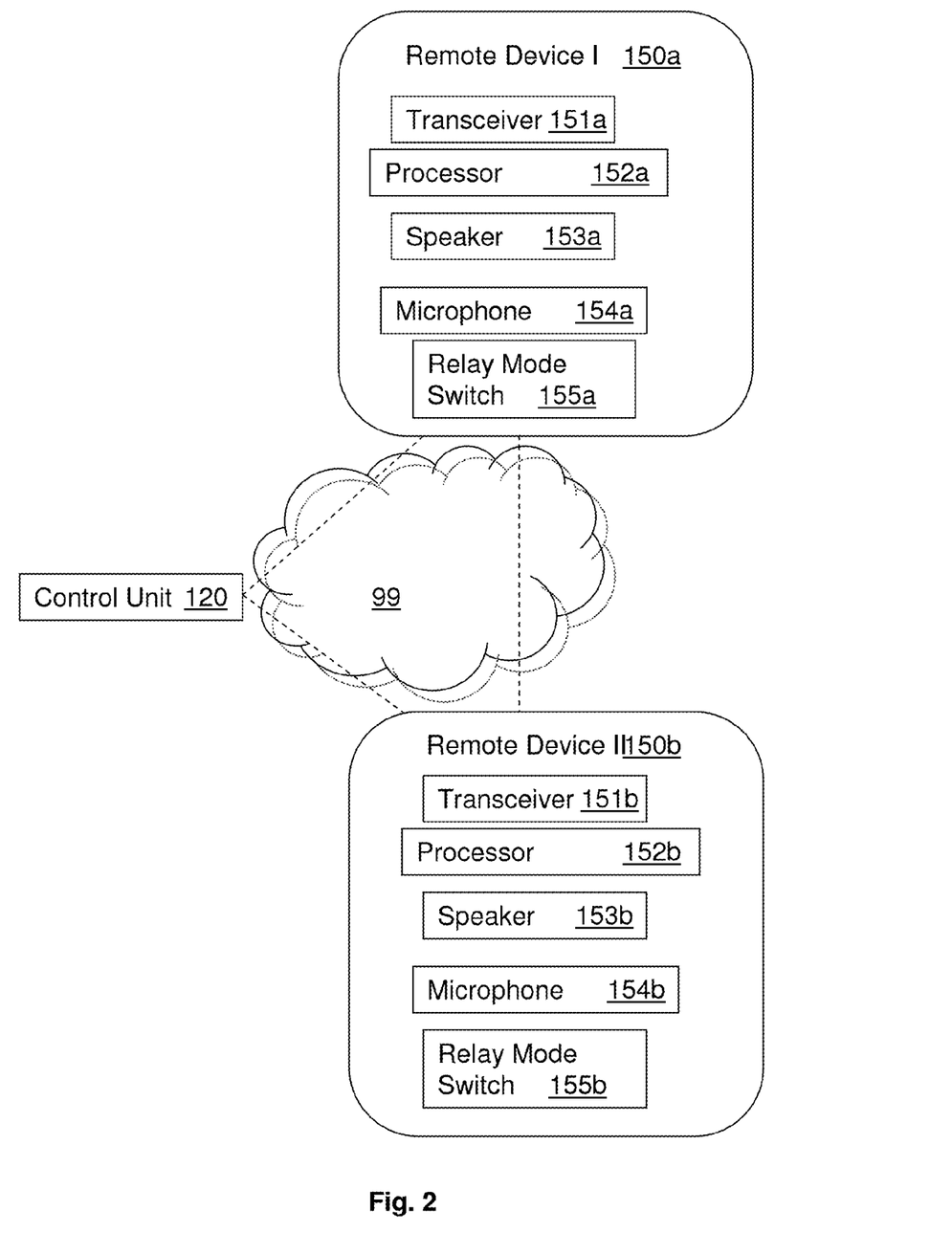
FIG. 2 schematically shows optional components of the remote devices of FIG. 1, according to some embodiments of the present invention.

According to some embodiments of the present invention, as illustrated in FIG. 2, each remote device 150*a*/150*b*, respectively, includes: (i) a transceiver 151*a*/151*b* for transmitting and receiving signals/data over one or more wireless communication channel such as RF channel 99 from and to control unit 120 and one another; (ii) a processor 152*a*/152*b* for processing the signals/data received; (iii) an audio output device such as a speaker 153*a*/153*b*; (iv) an audio receiver such as a microphone 154*a*/154*b*; and (v) a relay mode switch 155*a*/155*b*.

Transceiver 151*a*/151*b* may include a transmitter and receiver configured for receiving and transmitting signals over the respective wireless communication channel 99 such as, for example, transceivers for receiving and transmitting RF signals of a predefined RF band defining thereby the one or more communication channels system 100 can use.

According to some embodiments, relay mode switch 155*a*/155*b* allows the user to define the respective remote device 150*a*/150*b* as a relay station. This switching is received by processor 152*a*/152*b*, which may include an electronic circuit and/or digital card enabling to control all functionalities and processing of the respective remote device 150*a*/150*b*. Once in a relay mode, processor 152*a*/152*b* enables transmission of signals received from control unit 120 to be forwarded directly to the other remote device 150*b*/150*a* and/or transmitting signals such as audio signals arriving from the other remote device 150*b*/150*a* to control unit 120, serving thereby as a relay station of control unit 120 and/or the other remote device 150*b*/150*a*, thereby extending the range of talkback to the subject as well of the caretakers, users of remote devices 150*a* and 150*b*.

According to some embodiments, the relayed signal, received from control unit 120 by the relaying remote device 150*a*/150*b* may be amplified and/or cleaned (e.g. by reducing it signal-to-noise ratio using electronic means embedded in processor 152*a*/152*b* respectively) before transmitted to the other remote device 150*b*/150*a*.

The relay mode is especially yet not exclusively useful if the transmission range requirements are high—meaning a long range transmission is required requiring an intense transmitted signal. For example, the average longest distance between rooms in households or apartments in some countries such as the United States is quite high (e.g. over 50 meters) requiring the signal outputted by the control unit that is placed near the baby's bed to be quite high when compared with signal intensities of other wireless transmitting devices such as mobile phones and the like, which may be hazardous to the baby's health. In this case the relay feature allows using a much lower signal intensity outputted by the control unit that is located near the bed, covering a significantly smaller/shorter transmission range, since the remote devices can expand that range by relaying the signal. In this configuration, the relaying remote device is closer to the control unit than the other remote device(s) which receive the relayed signals.

Figure 3:
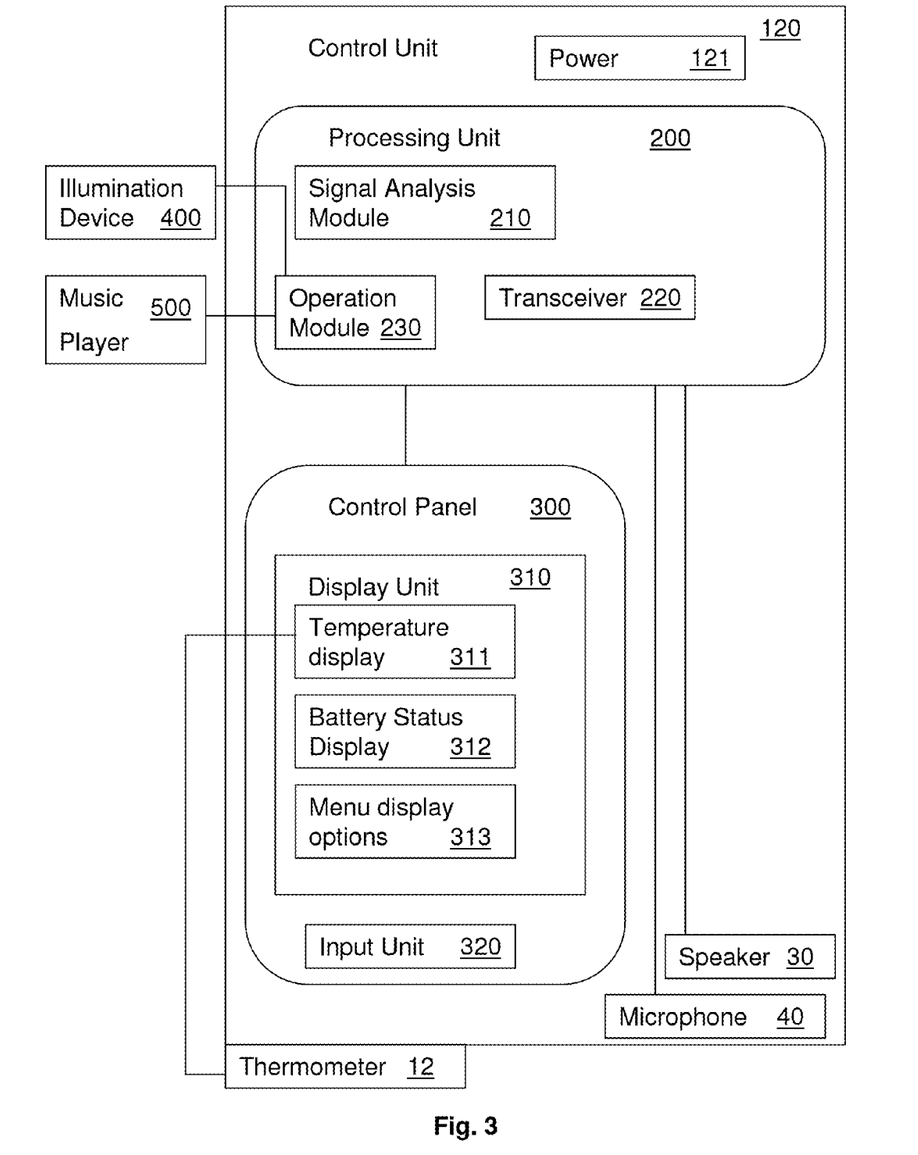
FIG. 3 schematically shows components of control unit of FIG. 1, according to some embodiments of the present invention.

Reference is now made to FIG. 3, which schematically shows components of control unit 120, according to some embodiments of the present invention.

Control unit 120 includes: a power source 121 such as a battery pack, a processing unit 200, a control panel 300, an audio output device such as a speaker 30, and an audio receiver such as a microphone 40. Processing unit 200 may include hardware means such as one or more electronic circuits and/or one or more digital cards for processing signals data received from sensor unit 110 and optionally also from microphone 40, power source 121 and the like.

As illustrated in FIG. 3, processing unit 200 includes a signal processing module 210, which may include hardware and/or software components. According to some embodiments, signal processing module 210 analyzes output signals received from sensor unit 110 to allow identification of breathing related alarming situations such as breathing cessation (no-breathing situations) and/or rapid breathing situations for determining whether a breathing alarming situation occurs in real time, which type of alarming situation and for operating alarm features predefined in control unit 120. for example, signal processing module 210 includes two predefined breathing related alarm situations and respective processes and conditions that allow identification thereof: (a) a first "no-breathing" alarming situation which can be identified if the output signal from sensor unit 110 does not exceed a predefined amplitude threshold level consecutively over a predefined time interval (typically for human subject such as babies for over 20 sec); and (b) rapid breathing situation in which the frequency of the output signal is higher in a substantially consecutive manner than a predefined frequency threshold value. In each such breathing related alarming situation an audio alarm may be operated by signal processing module 210 by operating a predefined sound alarm (of a predefined audio signal), using speaker 30. Optionally, each type of breathing related alarming situation is associated with a different sound alarm signal allowing the user to distinguish between the two alarming situations upon hearing the respective sound alarm.

According to some embodiments of the present invention, signal processing module 210 additionally allows identification and registering of presence periods by identifying placement and removal signal patterns of the output signals of sensor unit 110 indicative of the time periods in which the subject has been placed (laid) upon sensor unit 110, and/or according to the breathing pattern of the signal, as specified above. Each such identified period may be saved by and in processing unit 200 along with additional associated information such as time related information such as the date and hour of the day in which the respective placement and removal had occurred, and the like. These periods may then be displayed in a list display, using display device(s) of control panel 300 for allowing caretakers, for example, to monitor sleeping periods of a baby they are monitoring. This may also allow parents, for instance, in case the subject is a baby or a toddler, treated by another caretaker such as a babysitter, to see when this other caretaker has placed the baby in bed (where sensor unit 110 is located) and for how long. According to some embodiments, the placement ("in bed") and removal ("out of bed") signals may further be used to automatically turn system 100 or just sensor unit 110 on and off, respectively.

As illustrated in FIG. 3, processing unit 200 additionally includes a transceiver 220 for allowing communication with remote devices 150*a* and 150*b*. Transceiver 220 may enable communication over the same frequency band as the band enabled by transceivers 151*a* and 151*b* of remote devices 150*a* and 150*b*, respectively and optionally enable transmission of wireless signals of lower intensity than that of each of transceivers 151*a*/151*b* for emitting the lowest electromagnetic radiation possible in an area that is in proximity to the subject, especially, yet not exclusively if remote devices 150 and 150*b* enable the relay mode and depending upon transmission range requirements.

According to some embodiments, processing unit 200 additionally amplifies each signal received from sensor unit 110 and optionally cleans the signal (by reducing signal-to-noise ratio) for better analysis thereof.

According to some embodiments of the present invention, control unit 300 includes a display unit 310 configured for displaying various optional features such as monitored characteristics related information, battery status, menu options and the like and an input unit 320, for allowing users to input and set various system 100 features and modes. For example, display unit 310 includes a Liquid Crystal Display (LCD) screen enabling constant visual displaying of battery status using a designated power status indicator 312 and menu display 313 allowing indication of monitored related information such as alarm indications if and when such alarms are operated, breathing monitoring indication indicating that the breathing is monitored, and the like, According to some embodiments, some visual indications may be carried out using additional indication devices such as light-emitting-diode (LED) indicator lamps and the like, embedded in control unit 120.

According to some embodiments of the present invention, input unit 320 may include a panel including keys and/or buttons for allowing the user to set various features of system 100 such as switching buttons used for turning system 100, sensor unit 110, illumination device 400 and/or music player 500 on/off, set music player 500 and/or illumination device 400 features such as dimming level, music player volume level and the like.

Additionally and optionally, input unit 320 allows the user to define transmission related features such as transmission mode of control unit 120 (e.g. low or high options defining the intensity of the transmission signal), channel selection allowing the user to select one of a multiplicity of predefined wireless communication channels (frequency bands) enabled by transceiver 220, and the like. All of the above features may also be operated remotely from the remote devices.

According to some embodiments of the present invention, a thermometer 12 may be connected or embedded to/in control unit 120 for allowing measuring temperature in an area of control unit 120 and therefore an area that is near the subject's environment (e.g. in the baby's bed area). The measured temperature may be displayed over thermometer 12 and/or over display area 310 in a designated temperature display 311 over screen thereof that constantly shows the currently measured temperature.

Optionally, input unit 320 allows the user to define/set the units in which the temperature is displayed, where processing unit 200 allows converting the output of thermometer 12 into the selected units (e.g. converting Fahrenheit degrees into Celsius degrees and vice versa).

According to some embodiments of the present invention, breathing related alarms may be outputted only at control unit 120, using speaker 30, where the sound alarm outputted by speaker 30 is detected by microphone 40 allowing remote devices 150*a* and 150*b* to output these sound alarms by receiving the detected alarm sound through the signals transmitted by control unit 120 over the wireless communication channel 99 and outputting thereof using speakers 153*a* and 153*b* thereof. Alternatively or additionally, the transmitted signal may include both the sound data detected by microphone 40 as well as another signal indicative of the alarming situation allowing thereby each respective remote device 150*a* and 150*b* to output the audio alarm indication (sound alarm) as detected by microphone 40 to be outputted by speakers 153*a* and 153*b* as well as a visual indication of the alarming situation using, for example, LED indicator lamps embedded in remote devices 150 and 150*b*.

According to some embodiments of the present invention, control unit 120, and remote devices 150a and 150b enable transmitting and receiving signals over a multiplicity of predefined wireless communication channels each corresponding to a different frequency band. For example, system 100 enables synchronization between the transmission and receiving channels of control unit 120 and remote devices 150a and 150b.

According to some embodiments, once the relay mode is chosen in on of remote devices 150a or 150b the device intended to function as the relay unit sends an indication signal to control unit 120 as well as to the distant (not relay) remote device 150b/150a, to mark the information sent from these units with a header. A packet of bits consisting of a header that indicates that the attached information is intended to the distant remote device 150b/150a is sent from control unit 120 and thus the relaying remote device 150a/150b knows to transfer it to the distant one and vice versa (data sent from the distant remote device 150b/150a is marked to be transferred to control unit 120).

Figure 4:
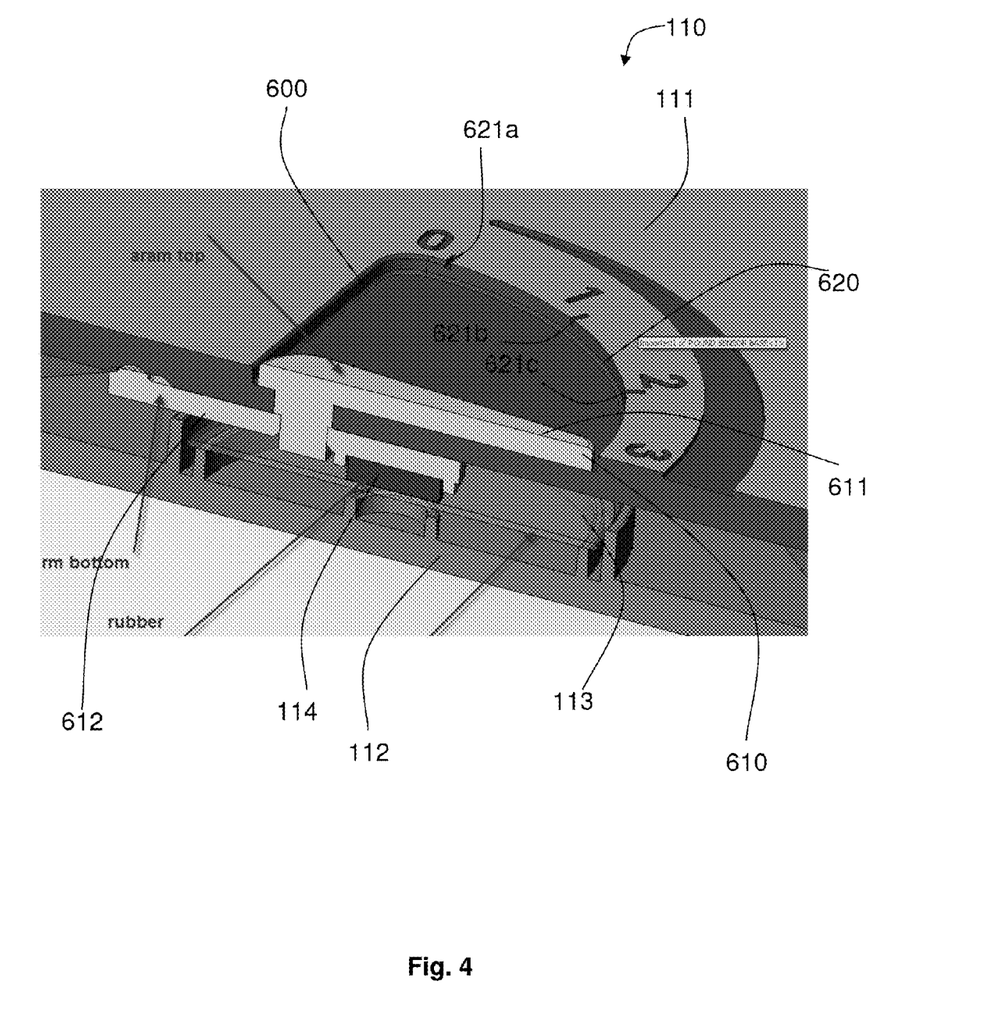
FIG. 4 schematically illustrates a sensor unit having a mechanical adjustment mechanism, according to some embodiments of the present invention.

Reference is now made to FIG. 4, which schematically illustrates sensor unit 110 connected to a mechanical adjustment mechanism 600, according to some embodiments of the present invention. According to these embodiments, sensor unit 110 includes an upper plate 111, a lower plate 112, a piezoelectric transducer 113 and an abutting element 114. Upper plate 111 is located underneath the subject's mattress and receives movements therefrom associated with movements of the subject lying over the mattress. Upper plate 11 connects to a much smaller abutting element 114, which is configured for abutting an upper surface of piezoelectric sensor 113 whenever a force is applied thereupon, originating from forces applied by the subject over upper plate 111. Piezoelectric transducer sensor 113 is attached to lower plate 112.

The surface area of upper plate 111 is significantly larger than the surface area of abutting element 114 thereby allowing the force F caused by the pressure P applied over the area of upper plate A by the subject to be transferred via a smaller impact (abutment) area a of abutting element 114 to the surface of piezoelectric transducer sensor 113, which in turn, translates this force into an electric signal.

As illustrated in FIG. 4, mechanical adjustment mechanism 600 includes a mechanical adjustor 610 that mechanically connects to abutting element 114 and allows thereby connecting abutting element 114 to upper plate 111 and a manual adjustment device 620 for allowing the user to manually adjust the sensitivity level of sensor 111 by mechanically displacing abutting element 114, in respect to the center of the surface of piezoelectric transducer sensor 113.

As shown in FIG. 4, mechanical adjustor 610 includes an upper member 611 and a lower member 612. Upper member 611 may be a handle integrally connected to an elongated lower member 612, where lower member 612 connects to abutting element 114. Mechanical adjustor 610 is pivotally connected to upper plate 111, where the positioning of piezoelectric transducer sensor 113 is constant and unchangeable, in relation to upper plate 111. This configuration forces abutting element 114 to change its location in respect to the center of piezoelectric transducer sensor 113 when upper member 611 is rotated by the user or by any other mechanical mechanism connected thereto.

As illustrated in FIG. 4, manual adjustment device 620 includes an adjustment scale, which is a depression in upper plate 111 that includes scaling indicators, which may include stoppers such as 621a, 621b and 621c that allow releasably fixating the handle upper member 611 therein to allow discrete adjustment of the sensor sensitivity.

According to other embodiments of the present invention, mechanical adjustment mechanism 600 additionally or alternatively allows the user to adjust sensor sensitivity by using control panel 320 of control unit 120, where an electronic mechanism operatively connects to mechanical adjustment mechanism 600. This will allow the user to adjust the sensor sensitivity without having to lift the baby's mattress in order to reach the upper plate of the sensor unit, for example.

According to additional or alternative embodiments of mechanical adjustment mechanism 600, mechanical adjustor 610 may additionally or alternatively connect to a shaft (Not Shown) rotatable by a motor (Not Shown), all components of mechanical adjustment mechanism 600, where the motor can be operated through control unit 120 for remote and easy sensitivity adjustment.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

What is claimed is:

1. A system for monitoring breathing related characteristics of a subject, said system comprising:
   (i) a sensor unit comprising an upper plate, a lower plate, a transducer sensor located over an inner side of said lower plate facing an inner side of said upper plate, and an abutting element, which is movably connected to the inner side of said upper plate facing a surface of said transducer sensor for abutting it correspondently to forces applied upon said upper plate, wherein said subject applies force upon said upper plate when laying thereover and thereby enables said upper plate to apply a mechanical force upon said transducer sensor via said abutting element, said force corresponds to breathing movements of said subject, said transducer outputs electric signals that correspond to said applied force;
   (ii) a control unit, which receives signals from said sensor unit indicative of movements of said subject, analyzes said signals to identify breathing related alarm situations and operate at least one alarm upon identification of said alarming situation; and
   (iii) a mechanical adjustment mechanism connected to said abutting element, for enabling a user to adjust sensitivity of said transducer sensor by mechanically adjusting the location of said abutting element in relation to an effective area of said transducer sensor, wherein sensitivity is decreased when said abutting element is distanced from said effective area, wherein said mechanical adjustment mechanism comprises a mechanical adjustor that mechanically connects to said abutting element and a manual adjustment device mechanically connected thereto for allowing the user to manually adjust the sensitivity level of said transducer sensor by moving said manual adjustment device, wherein said mechanical adjustor includes an upper member and a lower member connected to one another, wherein said lower member connects to said abutting element and said mechanical adjustor pivotally connects to said upper plate,
   wherein the positioning of the transducer sensor is constant and unchangeable, in relation to said upper plate, and
   wherein said abutting element changes its location in respect to the center of the transducer sensor when said upper member is rotated thereby allowing changing the respective location of said abutting member in relation to said effective area of said transducer sensor and thereby adjust sensitivity of said transducer sensor to forces applied upon said upper plate by the subject.

2. The system according to claim 1, wherein said manual adjustment device comprises an adjustment scale, which is a depression in upper plate that includes scaling indicators, which also includes stoppers that allow releasably fixating the a handle of the upper member therein to allow discrete adjustment of the transducer sensor sensitivity.

3. The system according to claim 1, wherein said mechanical adjustment mechanism further comprises a shaft connected to said mechanical adjustor for rotating thereof, and a motor, which allows rotating said shaft for allowing displacement of said abutting element, said motor is controllable through said user.

* * * * *